United States Patent [19]
Alt

[11] Patent Number: 6,076,014
[45] Date of Patent: Jun. 13, 2000

[54] CARDIAC STIMULATOR AND DEFIBRILLATOR WITH MEANS FOR IDENTIFYING CARDIAC RHYTHM DISORDER AND CHAMBER OF ORIGIN

[75] Inventor: Eckhard Alt, Ottobrunn, Germany

[73] Assignee: Sulzer Intermedics, Inc., Angleton, Tex.

[21] Appl. No.: 08/904,851

[22] Filed: Aug. 1, 1997

[51] Int. Cl.[7] .............................. A61N 1/362; A61N 1/39
[52] U.S. Cl. ...................................................... 607/4; 607/5
[58] Field of Search ............................................. 607/4, 5

[56] References Cited

U.S. PATENT DOCUMENTS

| | | |
|---|---|---|
| 5,433,729 | 7/1995 | Adams et al. . |
| 5,472,453 | 12/1995 | Alt .............................................. 607/4 |
| 5,690,686 | 11/1997 | Min et al. .................................. 607/5 |

*Primary Examiner*—William E. Kamm
*Assistant Examiner*—Carl H. Layno
*Attorney, Agent, or Firm*—Blank Rome Comisky & McCauley LLP

[57] ABSTRACT

A medical interventional device is structured for implantation in a human patient, to respond to detection of cardiac activity of the patient indicative of cardiac dysrhythmias. The device includes a cardiac therapy system responsive to a detected arrhythmia in either the atrial or ventricular chambers for automatic therapeutic treatment by selective application of an appropriate therapy regimen consisting of pacing, cardioverting or defibrillating waveforms of predetermined type and energy content to the chamber diagnosed as that in which the dysrhythmia originated. The device incorporates a DDD or DDD-R pacemaker for dual chamber sensing of electrical (ECG) activity, and for constant pacing of the atrium and atrioventricular synchronization. A fuzzy logic subsystem is used for diagnosis including identification of the originating heart chamber. The electrode system for delivering the selected therapy regimen includes a single lead for pacing, sensing, cardioversion and defibrillation associated with each of the right atrial and ventricular chambers. A counter-electrode for defibrillation may be the metal case in which the device electronics are housed, or a cardiac electrode implanted in the left pulmonary artery or the distal coronary sinus.

25 Claims, 2 Drawing Sheets

CARDIAC STIMULATOR AND DEFIBRILLATOR WITH MEANS FOR IDENTIFYING CARDIAC RHYTHM DISORDER AND CHAMBER OF ORIGIN

BACKGROUND OF THE INVENTION

The present invention relates generally to implantable medical interventional devices and methods for treating cardiac rhythm disorders, and more particularly to an implantable defibrillator for ventricular defibrillation, with pacing and sensing of the atrium and related methods of therapy using such implantable defibrillators.

Current implantable defibrillators perform a variety of functions designed to treat ventricular arrhythmias, including sensing of ventricular signals, detection of ventricular arrhythmias consisting of bradycardia, tachycardia, and fibrillation, and delivery of appropriate therapy automatically selected from among bradycardia and antitachycardia pacing, cardioverting and defibrillating shocks of the ventricles to correct the disorder. A serious problem with these devices is that a significant percentage of the defibrillating shocks delivered to the ventricles—about 25%—are falsely fired, delivered while the patient is fully conscious. The statistic is supported by recordings of cardiac activity among patients whose implanted devices have Holter function capabilities, and study of the recorded time period immediately before and up to delivery of the defibrillating or cardioverting shock, as well as by numerous interviews of defibrillator patients. Aside from the extreme pain suffered from a false shock, the patient tends to quickly lose confidence in the reliability of the implant as a life-saving device.

A large part of the reason for the false shocking is that many patients develop atrial fibrillation and atrial flutter spontaneously, and, with a tendency for fast conduction through the atrioventricular (AV) node, the ventricle is driven at a high rate. If the ECG criteria for ventricular tachycardia or fibrillation on which the implanted device relies for performing its therapy functions are fulfilled, a high energy cardioverting or defibrillating shock will be delivered to the ventricle. The shock—albeit false—is a proper response, given the criteria from which the determination was made. Rather, it is the data on which this response is based that is insufficient.

The solution to this problem of intermittent atrial fibrillation and flutter that can give rise to false shocks is to give greater attention to the status of the atrium. Currently available implantable defibrillator devices are unable to provide the solution because their focus is on the status of the ventricle. Recognition of atrial activity together with that of ventricular activity enables better discrimination of sinus rhythm, sinus tachycardia, ventricular fibrillation and ventricular flutter from one another. The better discrimination of the dysrhythmia—or absence thereof—allows the device to more properly respond with a corrective therapy that is based on the true condition of the patient. In other words, the device can better distinguish which heart chamber is attributable to the arrhythmia, so as to respond in kind.

It is a principal aim of the present invention to provide an implantable defibrillator that monitors the atrial status as well as the ventricular status, to discriminate arrhythmias of atrial origin from arrhythmias of ventricular origin, from which to better select the proper electrical therapy to be delivered to the patient's heart, and more specifically, to eliminate or at least substantially lessen the likelihood of false shocking.

Another problem which is not solved by the currently available spate of implantable defibrillators is the prominence of atrial arrhythmias which occur in implant patients because of a failure to address the atrial chamber. For example, the current devices perform ventricular pacing, but if retrograde conduction occurs the patient has a relatively high risk—40% or more—of developing atrial fibrillation. In contrast, patients who are experiencing constant atrial stimulation along with the ventricular pacing have a much lower risk—on the order of 5 to 10%—of developing intermittent or chronic atrial fibrillation.

Accordingly, another aim of the present invention is to provide an implantable defibrillator that performs pacing of the atrium as well as the ventricle, so as to enable better prevention of atrial arrhythmias.

SUMMARY OF THE INVENTION

According to one aspect of the present invention, an implantable defibrillator possesses the usual capability of ventricular defibrillation along with ventricular bradycardia and tachycardia pacing, and sensing of the ventricular signals (i.e., ECG or cardiac signals) for determination of which of those therapies is to be delivered, but also performs stimulation of the atrium. Specifically, the device has the capability to pace the atrium to assure a constant or continuous rate of depolarizations, e.g., whether spontaneous (intrinsic, i.e., triggered by electrical activity of the sinoatrial (SA) node) or paced (i.e., stimulated, in the absence of such intrinsic activity, by operation of the implanted device). This type of atrial pacing assures that AV synchrony will be maintained, i.e., ventricular depolarizations are continuously synchronous with atrial depolarizations as a consequence of ongoing depolarizations of the atrium at the specified rate, with each atrial beat followed sequentially by a ventricular beat, under conditions in which the device is not called on to provide other therapies of a priority hierarchy that necessitate a different stimulation of the atrium such as antitachycardia pacing or cardioversion or defibrillation.

This fallback or "default" condition of continuous stimulation of the atrium at a fixed pacing rate by the implanted defibrillator device serves to significantly reduce the incidence of atrial arrhythmias, and can also reduce or even eliminate dependence of the patient on prescribed antiarrhythmic medications or beta-blockers. Further, the assured synchronization of the atrial and ventricular contractions of the heart represents a hemodynamic improvement for many patients who are candidates for an implantable defibrillator, by which the overall cardiac performance of these patients is improved to an extent that additionally aids in reducing the occurrence of dysrhythmias.

In addition to pacing the atrium at a fixed rate which is appropriate for the particular patient who is to receive the implant, the defibrillator device is provided with a capability to sense the atrial rhythm, i.e., the atrial signal, independently of the ventricular signal. By doing so, and applying appropriate algorithms which compare the atrial and ventricular status, the implanted device can provide a more precise diagnosis of the nature of the underlying rhythm disorder. For example, if ongoing ventricular tachycardia is detected by the implanted device, the presence of normal sinus rhythm at the atrial sense signal input facilitates a diagnosis that the tachycardia is of ventricular origin. On the other hand, if the device senses ventricular tachycardia while the atrial sense signal reveals atrial flutter or atrial fibrillation, the origin of the rhythm disorder is determined to be in the atrium with a fast ventricular response.

Since both atrial and ventricular pacing are employed, as well as atrial and ventricular sensing, the implantable device of the invention effectively combines the advantages of DDD pacing with a conventional "full function" defibrillator, which as noted above, generally includes brachycardia and tachycardia pacing of the ventricle and cardioversion and defibrillation of the ventricle. DDD, of course, is part of the three-position ICHD (Inter-Society Commission on Heart Disease Resources) device code which indicates that the device is adapted to provide dual chamber pacing, dual chamber sensing, and both triggered and inhibited modes of response (atrial triggered and ventricular inhibited).

It is also desirable to provide the device with a rate adaptive or rate responsive capability which enables it to recognize whether the patient is engaged is resting or engaged in exercise, which is then used to adjust the rate according to the nature and extent of the exercise, and can also be taken into account in diagnosing whether a rhythm disorder is present (for example, in assessing whether a tachycardia is physiologic or pathologic). In a preferred embodiment, the invention employs a two-dimensional accelerometer as a sensor of activity and position of the patient. Thus, the DDD pacemaker with which the defibrillator is combined becomes a DDD-R (the "R" suffix being indicative of rate adaptive capability in the ICHD device code).

Atrial monitoring, detection and treatment which are effective to terminate an arrhythmia have the added benefits of lower energy dissipation and greater likelihood that treatment will be administered while the patient is conscious (with consequent easing of the task of successful treatment), compared to treating arrhythmias of ventricular origin. For example, atrial flutter is broken by rapid atrial stimulation and atrial fibrillation is terminated by applying a defibrillating shock to the atrium—to synchronize the atrium—using virtually the same antitachycardia or defibrillator subsystem as that for treating ventricular tachycardia and fibrillation, except that the energy requirements are significantly lower and can be tolerated by the conscious patient without significant pain.

According to another aspect of the invention, further improvements in diagnosis and treatment are obtained in a preferred embodiment by the use of fuzzy logic, which examines the extent to which a particular finding is true or false, allowing the decision on appropriate therapy to be made without regard to non-linearity of the findings. Determinations and selections are made according to the degree of membership of a particular statement (a finding) has to a certain class (e.g., the extent of truth or falsity of the finding).

Another feature of the invention is that the number of leads to be implanted for use with the device is reduced, with attendant simplification of surgical procedure and reduction of cost, because the same lead may be used for atrial and ventricular pacing, sensing and defibrillation. Two transvenous leads having a size of about 6½ French may be employed, with pacing/sensing cathodal tip and sensing/pacing/shocking anodal ring for conventional bipolar pacing and sensing, and low polarization electrodes for shocking to allow intrinsic rhythm to be detected without masking by polarization currents.

Other aims of the invention, then, are to provide an implantable device that combines the capability for ventricular pacing, sensing and defibrillation with a DDD or DDD-R pacing capability to improve detection, diagnosis, and treatment of arrhythmias, including origin as being atrial or ventricular; provision of rate adaptive capability for both pacing rate adjustment according to activity and improved diagnosis of arrhythmias; use of fuzzy logic to simplify and enhance diagnosis and treatment; and capability to use fewer leads for device implantation.

In U.S. Pat. No. 5,243,980, an automatic cardioverter/defibrillator (ACD) is disclosed as having the capability to discriminate ventricular tachycardias from supraventricular tachycardias, and to distinguish sinus tachycardias from non-sinus tachycardias. The device electrically stimulates fat pads associated with the SA node and AV node, as part of the nervous system that regulates the rhythm of the heart. The device of the '980 patent detects a ventricular tachycardia and then stimulates the nodal fat pads in synchronism with detected atrial depolarizations and/or ventricular depolarizations. The origin of a tachyarrhythmia is determined from an observation of which fat pad, when stimulated, induces a predetermined change in the cardiac rhythm. If no change in the ventricular rate is observed upon stimulation of either fat pad, the ventricle is deemed the origin; whereas if the atrial rate or the ventricular rate decreases, depending on which fat pad is stimulated, the tachyarrhythmia is deemed to be supraventricular in origin, or a sinus tachycardia. Although the '980 patent describes an implantable pacemaker/cardioverter/defibrillator including possible DDD pacing, neither the type of pacing nor the identification of rhythm disorders corresponds to that of the present invention. Rather, the fat pad stimulation technique is employed.

BRIEF DESCRIPTION OF THE DRAWINGS

The above and still further aims, aspects, features and attendant advantages of the present invention will become apparent from a detailed description of the best mode presently contemplated for practicing the invention, with reference to certain preferred embodiments and methods, in conjunction with the accompanying drawings, in which.

DESCRIPTION OF THE PREFERRED EMBODIMENT AND METHOD

Figure 1:
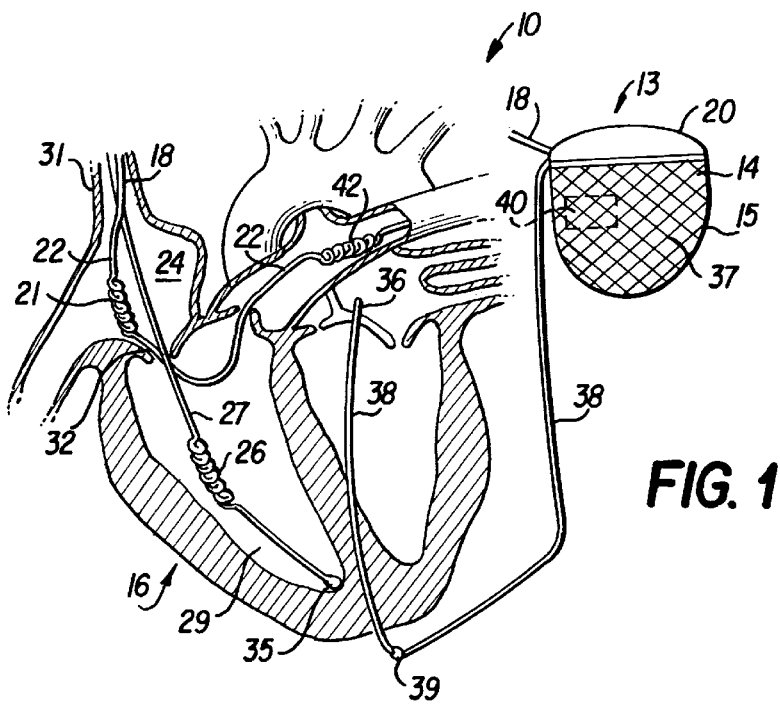
FIG. 1 is a cutaway view of the patient's heart showing placement of signal generator and associated cardiac leads and electrodes of the implanted defibrillator, according to an embodiment of the invention.

Referring to FIG. 1, a medical interventional device such as implantable defibrillator 13 includes a signal generator 14. The generator is implanted in a surgically-formed pocket in the flesh of the patient's chest 10, or other desired location of the body. Signal generator 14 is conventional except as will otherwise be described herein, incorporating electronic components for performing signal analysis and processing, waveform generation, data storage, control and other functions, power supply (battery or battery pack), which are housed in a metal case (can) 15 compatible with the tissue and fluids of the body (i.e., biocompatible). The device is microprocessor-based with substantial memory, logic and other components to provide the processing, evaluation and other functions necessary to determine, select and deliver appropriate therapy including electrical shocks and pulses of different energy levels and timing for ventricular defibrillation, cardioversion, and pacing to the patient's heart 16 in response to cardiac dysrhythmias including ventricular fibrillation (VF), ventricular tachycardia (VT), and ventricular bradycardia.

Composite electrical lead 18 which includes separate leads 22 and 27 with distally located electrodes is coupled at the proximal end to signal generator 14 through an electrical connector 20 in the header of case 15. Preferably, case 15 is also employed as an electrode such as electrical ground, for unipolar sensing, pacing or shocking. Unlike the defibrillator devices of the prior art, the signal generator and lead(s) of the present invention are implemented for atrial sensing, pacing and shocking as well as the ventricular functions. Defibrillating shocks of appropriate energy level are applied between the case and electrode 21 on lead 22 implanted in the right atrium 24 through the superior vena cava (SVC) 31, or between the case and electrode 26 on lead 27 implanted through the SVC in the right ventricle 29, for treating atrial fibrillation (AF) or VF, respectively. Leads 22 and 27 and their associated distal tip electrode 32 (to a separate conductor) and distal tip electrode 35 (also to a separate conductor within the lead), respectively, are used for both sensing and pacing cardiac activity in conjunction with the circuitry of signal generator 14. To that end, electrode 32 is positioned in the right atrium against either the lateral or anterior atrial wall thereof, and electrode 35 is positioned in the right ventricle at the apex thereof. Active or passive fixation of the electrodes may be used to assure suitable excitation. Tip electrode tip 35 preferably has a standard 4 to 8 millimeter (mm) configuration, and is provided with soft barbs (tines) to stabilize its position in the ventricle. Each of the electrodes, those used for defibrillation and cardioversion, as well as those used for sensing and for pacing, are electrically connected to separate conductors in leads 22 and 27.

If desired, rather than simply using metal case 15 as an electrode, a conductive pouch 37 comprised of a braided multiplicity of carbon fine, individual, predominantly isotropic wires such as described in U.S. Pat. No. 5,143,089 to the applicant herein is configured to receive, partly enclose and maintain firm electrical contact with the case. This serves to enhance the effectiveness of the anodal electrode of the case and establish a better vector for the electric field produced by the defibrillation shock waveform, and thereby lower the defibrillation threshold. The conductive pouch can be electrically connected directly to an extension lead 38 composed of similar carbon braid of about 7 french diameter which is implanted subcutaneously for connection to an epicardial or pericardial patch electrode (not shown) or as a wire electrode (as shown) through an opening formed by puncture surgery at 39. The conductor for electrode 36 of lead 38 may be implanted subcutaneously to a point 39, and then by puncture surgery through the thoracic cage and the pericardial sac, under a local anesthetic. The lead 38 is run parallel to the sternum, through the puncture, and then through the patient's thoracic cage and into the pericardial sac. It may even be threaded through the thoracic cage, the pericardial space about the left ventricle and atrium, and back along the right atrial appendage, external to the heart. The distal end 36 of lead 38 is preferably placed close to the left atrium of the patient's heart to provide an increase in electric field strength and support the strong vector of the electric field according to the heart chamber to be defibrillated. Selection of the chamber (atrium or ventricle) which is to undergo defibrillation is made by choosing the appropriate endocardial counter-electrode (21 or 26, respectively) to be energized together with the carbon electrode, if the case 15 or conductive pouch 37 is not used directly as the other electrode.

Fabricating the electrode portion of conductor 38 (from the point of entry 39 into the thoracic cage) of carbon braid provides the desirable features described earlier herein. The path of conductor 38 and electrode 36 need not be as shown in the Figure, but rather as described immediately above. The positioning improves the vector for defibrillation through the atrium as well as the ventricle.

Atrial coil electrode 21 is used for bipolar sensing as well as a counter-electrode for atrial defibrillation or cardioversion shocking. Hence, electrode 21 is preferably also composed of a braided carbon fiber material described in the '089 patent, to take advantage of its very low polarization and low defibrillation threshold, to allow the intrinsic rhythm to be detected almost immediately after delivery of a shock for accurate determination of the current status of electrical activity of the atrium. The features of low polarization and accurate sensing are important for detection and evaluation of atrial status since atrial signals have magnitudes of only about 20% to 25% those of ventricular signals because of the smaller atrial mass. The braided carbon fiber structure of electrode 21 is also desirable to provide a large effective electrical surface area (for example, in a range from three to six square centimeters) relative to its considerably smaller geometric area, which provides greater energy efficiency for defibrillation.

As with atrial electrode 21, ventricular electrode 26 of lead 27 is positioned for use as a defibrillation electrode as well as for bipolar sensing in the ventricle. For defibrillation, electrode 26 also cooperates with the metal case 15, pouch electrode 37, or pericardial electrode 36, whichever of these latter electrodes is used in the defibrillator implementation. Again, a braided conductive structure for electrode 26 provides it with an effective surface area considerably larger than its actual exposed surface area. As an alternative, the electrode may be composed of fine metallic filaments and fibers of platinum iridium alloy, braided together to offer similarly desirable electrode characteristics.

Thus, the tip electrodes of leads 22 and 27 are used for sensing and pacing of the respective atrial and ventricular chambers as in a conventional DDD pacemaker, with dual-chamber pacing, dual-chamber sensing, and both triggered and inhibited response. Further, the defibrillator 13 uses a transvenous electrode for ventricular defibrillation and stimulation and an atrial bipolar lead for sensing and atrial defibrillation, so that atrial defibrillation is performed with one of the same electrodes used for atrial stimulation and sensing.

Rather than terminating at distal tip electrode 32, the latter electrode may be positioned at mid-lead of the atrial transvenous lead 22 which extends and is threaded through right atrium, ventricle, pulmonary valve, and into the left pulmonary artery, with a coil counter-electrode 42 connected to a separate conductor of the lead. With this alternative embodiment, a defibrillating shock waveform can be applied between electrode 42 and atrial defibrillation electrode 21 upon detection of atrial fibrillation. In that configuration, electrode 42 would replace signal generator case 15, conductive pouch 37, or lead portion 36 as the selected electrode, and enables a strong vector for the electric field through right and left atrium. Rather than placement in the left pulmonary artery, electrode 42 may be positioned in the distal coronary sinus for defibrillation of the atrium in conjunction with electrode 21.

Defibrillation of the atrium and ventricle is achieved by application of shock waveforms of suitable shape and energy content between appropriate electrodes, such as electrode 36 and electrode 21 for atrial fibrillation, or between electrode 42 and electrode 21 for atrial fibrillation; or between electrode 36 and electrode 26 for ventricular fibrillation, in which atrial electrode 21 can be used additionally as either anode or cathode. The case 15 can serve as the anode for delivery of the shock as well, and can provide ground reference potential for unipolar sensing and pacing, in both chambers.

In a preferred embodiment of the invention, the implantable defibrillator is provided with a rate-adaptive pacing capability by employing an accelerometer 40 as an activity sensor located on a hybrid electronic circuit (not shown) mounted within signal generator case 15. The hybrid electronic circuitry on which the accelerometer is located may include a micro-miniaturized silicon structure incorporating an electromechanical (or mechano-electrical) converting element as the accelerometer, as well as another or other devices secured thereto for performing other logic and electronic circuit functions for processing the sensor signal. A suitable structure is described, for example, in U.S. Pat. No. 5,031,614. The sensor detects movement or acceleration of the patient in the course of physical activity, which may simply be even a slight change in physical position. The accelerometer is preferably mechanically isolated from the wall of the case to avoid a false indication of physical activity as a result solely of pressure on the surface of the case itself In a rate-adaptive (DDD-R) pacing mode, the accelerometer sensor signal is used to control the rate at which pacing pulses are generated by the signal generator 14, to vary the pacing rate according to the patient's metabolic need and thus to improve hemodynamic performance, especially for patients with enlarged heart. The physical stress-dependent regulation of the heart rate improves the patient's exercise capacity, and the activity sensor-controlled variation of the atrial rate serves as a deterrent against atrial dysrhythmias. Therefore, the rate adaptation by means of a sensor that controls the pacing rate can serve to prevent fibrillation and thereby avoid or at least reduce the need for defibrillating shocks from the implanted device.

In addition to providing the rate adaptive pacing capability in the implanted device 13, accelerometer 40 also functions to provide information to confirm or reject a diagnosis or analysis of a dysrhythmia detected by the cardiac activity sensor(s). For example, the accelerometer may indicate that a tachycardia is physiologic versus pathologic, or vice versa, by evidencing that a sudden jump in heart rate is attributable to abrupt physical activity of the patient, or by indicating that a ventricular tachycardia is pathologic because it occurred at a time that the patient was resting. From the data confirming or rejecting a cardiac event, an appropriate evaluation and decision may be made as to whether the patient is experiencing a particular dysrhythmia, and, if so, identifying and selecting the most appropriate therapy to be delivered to return the patient's heart to normal cardiac rhythm. Additionally, the accelerometer may aid in demonstrating that a perceived ventricular dysrhythmia is in fact of atrial origin.

An evaluation of the accelerometer signal will determine whether a given atrial rate is adequate or inadequate. A conditional ventricular tracking limit is established so that the maximum achievable atrial triggered rate is controlled by the sensor, which is especially important to limit the ventricular rate response in cases where atrial arrhythmias would trigger an inappropriately high ventricular rate, as in a pure DDD pacemaker.

Figure 2:
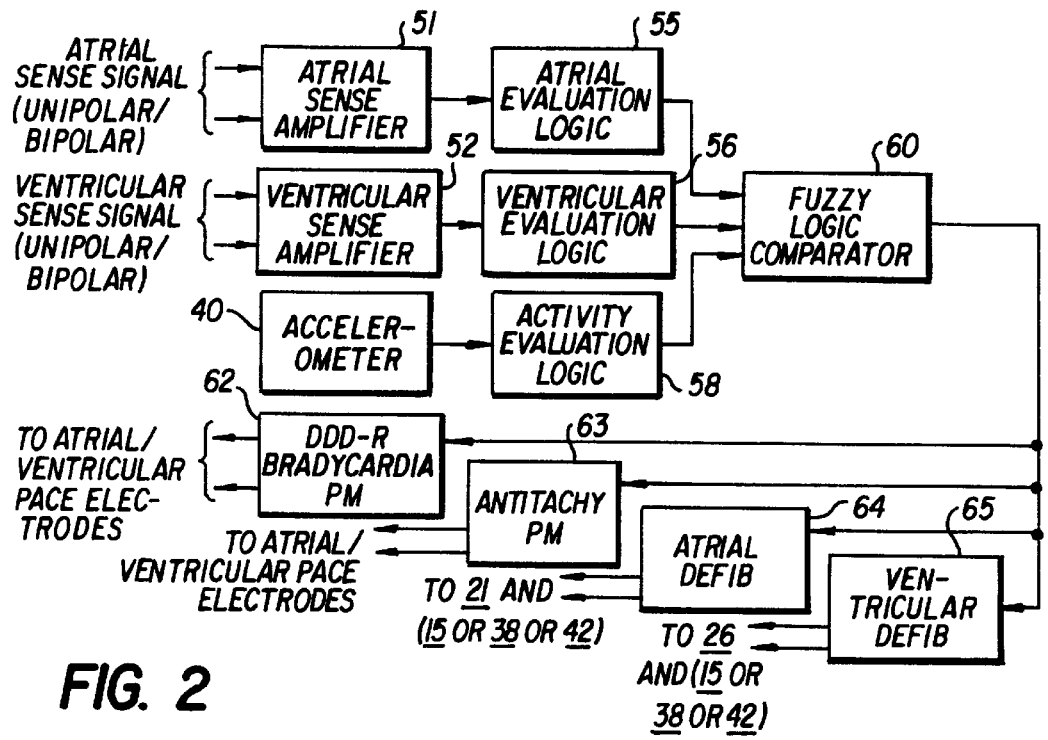
FIG. 2 is a functional block diagram of the signal generator illustrating lead/electrode connections.

FIG. 2 is a functional block diagram of signal generator 14. Cardiac activity (internal ECG) signals detected by tip electrodes 32 and 35 of atrial and ventricular transvenous leads 22 and 27 (or, for bipolar sensing, together with respective electrodes 21 and 26) are processed initially by sense amplifiers 51 and 52, respectively. Further processing of these signals is performed by atrial and ventricular evaluation logic 55 and 56, respectively; and separate activity evaluation logic 58 is used to process the activity output signal of accelerometer 40.

The signal information generated by the accelerometer indicates physical movement and physical position of the patient, as additional information about the status of the patient which can be used to confirm or reject the indicia supplied by the other sensors. For example, if the ventricular sense channel shows a fast ventricular rate and the accelerometer sense channel shows that the patient is not moving, the two pieces of data confirm the existence of a pathologic tachycardia, albeit the origin may be an atrial rhythm disorder. The latter can be confirmed or rejected by the signal information from the atrial sense channel. Thus, the non-ECG sense channel provides additional evidence for enhancing the determination of the nature and type of an arrhythmia detected by one or both of the ECG electrode sensors in the atrial and ventricular chambers of the heart.

Each evaluation logic circuit uses its input signal to develop a general finding or "statement" on the status of the respective sense channel. The statements may be, and typically are, imprecise. For example, atrial evaluation logic 55 may examine the processed signal from its sense channel and based on a comparison with a preset normal heart rate, may indicate that the atrial rate is normal (or fast, or slow). Similarly, ventricular evaluation logic 56 may make a determination from its criteria that the ventricular rate is fast. And the activity evaluation logic 58 may determine that the patient has commenced walking, from the immediately preceding condition of rest. Statements or findings such as these are supplied to a fuzzy logic comparator 60.

ECG criteria may be applied to diagnose atrial tachycardia, including, for example, sudden rate change, increase in rate over time, absolute atrial rate, rate stability, variation of cycle length of the individual atrial pulses, and variation of the atrial pulse amplitude. These same ECG criteria may be applied to discriminate stable atrial rhythms, which may be sinus rhythm, sinus tachycardia and sinus bradycardia, from irregularities in the atrium, which may be sinus arrhythmia, sinus arrest, ectopic atrial beats, atrial flutter and atrial fibrillation.

Fuzzy logic is somewhat imprecise, but provides a practical approach to decision-making based on the extent to which a statement is either true or false, i.e., the degree of membership to a particular class. If the statement is 100% true or 100% false, the decision is simple. Usually, however, the statement is partly true and partly false—for example, it may be 70% true and 30% false—so that the decision is less clear. Using fuzzy logic, a judgment is effectively based on how much a statement belongs to zero or one. The process is a type of bi-level logic in which the degree of membership in a statement is determined in a manner similar to a polling process. The fuzzy logic may be implemented in digital or analog circuitry, with very low power consumption. Fuzzy logic principles are reasonably well known, and no claim is made herein to the invention of fuzzy logic per se.

Fuzzy logic comparator 60 looks at the inputs derived from the three sense channels, and uses a predetermined set of rules or algorithms to govern which of a plurality of different therapies will be used to treat a perceived rhythm disorder. By application of appropriate algorithms which independently compare the atrial status, the ventricular status, and the physical activity status, the implanted defibrillator establishes an enhanced diagnosis of the nature of the underlying rhythm disorder; and this, in turn, leads to a more accurate selection of the proper therapy for treatment.

To apply the appropriate therapy to the individual arrhythmia condition as quickly and accurately as possible, several algorithms may be used for the decision-making. One very important feature of this aspect is not only to consider the momentary status of the atrial and ventricular rates and the ECG morphology, but also to incorporate into the decision process the historical trend and to compare it to the actual atrial and ventricular ECG signal with respect to cycle length, amplitude morphology vector, and cycle length stability.

For example, if the atrial rate is more than 300 beats per minute (bpm) and the cycle length varies more in comparison to atrial rates less than 150 bpm (quotient of mean cycle length divided by standard deviation of cycle length) and the mean atrial signal amplitude is less than the atrial signal amplitude with atrial rates slower than 150 bpm, then the conditions of atrial fibrillation are fulfilled. If the ventricular rate is between 120 bpm and 190 bpm and has changed in the same moment as a change observed in the atrial rate—in comparison to the historical trend—a fast ventricular response following enhanced AV nodal conduction to the atrial fibrillation is most likely, and therapy appropriate for atrial fibrillation is called for.

In another example, if the atrial rate exceeds 200 bpm to 350 bpm, and if the cycle length is relatively constant (i.e., the standard deviation from beat to beat is low in comparison to the mean of the cycle length), the amplitude of the atrial ECG signal is rather constant and not less than 50% of the atrial signal amplitude with sinus rhythm, then atrial flutter is diagnosed by the detection algorithm. Further confirmation of this diagnosis is established by consideration of the historical trend. A sudden change in atrial rate from one beat to another confirms the pathologic atrial status. In this case, the implanted defibrillator applies a burst or other form of rapid atrial stimulation as a therapeutic option to interrupt the tachycardia. The therapy of choice if the rapid pacing fails to break the atrial flutter is to apply a low energy atrial shock starting with about 0.3 joule, and to increase the energy with successive shocks until success is achieved.

A further example is if the ventricular rate fulfills the criteria of ventricular fibrillation and the physical activity sensor indicates sudden collapse (syncope) of the patient, which indicates compromised cerebral perfusion following a fast and irregular heart beat, then the defibrillator commences charging immediately to the maximum available energy to apply a ventricular defibrillating shock, irrespective of whatever the momentary atrial status may be.

By way of further example, stated in terms of a fuzzy logic diagnosis and therapeutic response, one rule may be: IF (ventricular rate is FAST .AND. atrial rate is NORMAL. AND. patient activity is SLOW) THEN (ANTITACHYCARDIA PACING of ventricle). The evaluation of a rapid ventricular rate in the presence of normal sinus rhythm in the atrium is diagnosed as a pure ventricular tachycardia, leading to selection of antitachycardia pacing therapy applied to the ventricle.

Another fuzzy logic rule may be: IF (atrial rate is FAST .AND. ventricular rate is FAST .AND. patient MOTIONLESS) THEN (DEFIBRILLATION of atrium). The evaluation of a rapid ventricular rate in the presence of a fast atrial rate while the patient is not moving, is diagnosed as a fast ventricular response to atrial flutter or atrial fibrillation, and as calling for the delivery of relatively low energy shocks (e.g., 5 joules or less) to the atrium from an atrial defibrillator or cardioverter.

This is in marked contrast to a typical response to the detection of a rapid ventricular rate by a conventional automatic implantable defibrillator, in which a high energy (e.g., exceeding perhaps 30 joules) shock may be delivered to the patient's heart despite the fact that the patient is experiencing only atrial flutter and is fully conscious. The false shock is not only painful, but serves no useful purpose in treating the underlying rhythm disorder. It may indeed exacerbate the problem by creating an environment conducive to true VF.

The therapy designated by the output signal of the fuzzy logic comparator 60 is delivered by the applicable portion of the signal generator, which may be for bradycardia pacing (DDD-R) 62, antitachycardia pacing 63, atrial defibrillation (or cardioversion) 64, or ventricular defibrillation (or cardioversion) 65. It will be readily understood that each of these therapy-delivering subsystems need not be entirely separate or distinct from one another, but may, and generally will, share components among one another.

If the therapy is successful to alleviate the detected rhythm disorder, the fuzzy logic comparator recognizes this state of affairs from the output signal information supplied by the evaluation logic circuits. For example, an appropriate rule may be: IF (atrial rate is NORMAL .AND. ventricular rate is NORMAL. AND. patient movement is DON'T CARE) THEN (MAINTENANCE). In this example, the specified maintenance may be to continue pacing the atrium at a constant rate and to synchronize the atrial and ventricular rates.

Figure 3:
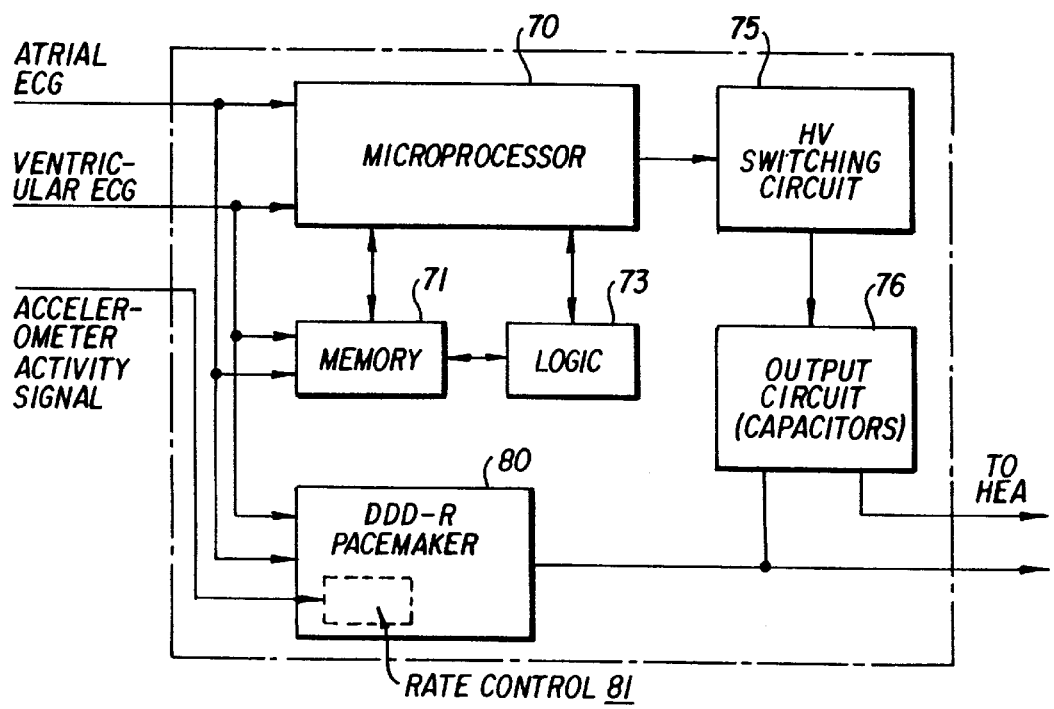
FIG. 3 is a simplified partial block diagram of the signal generator.

FIG. 3 is a simplified block diagram of a portion of the signal generator 14 of the implantable defibrillator illustrating component blocks used in treating pacing problems such as bradycardia and tachycardia, as well as in treating both atrial and ventricular fibrillation. Circuit details are minimized or omitted for the sake of convenience and clarity, such as signal conversion components. The subsystem includes a microprocessor 70 with associated memory 71 which may, for example, be volatile SRAM, for storing cardiac rhythm data from each of the atrial and ventricular ECG sensors. If an evaluation of the ECG sense signals by logic 73 indicates that the patient is experiencing fibrillation, the microprocessor 70 will activate switching circuit 75 to charge output storage capacitors 76 to a predetermined appropriate level for delivering a defibrillating shock waveform to the defibrillation electrodes for the designated chamber of the heart.

DDD-R pacemaker 80 is also responsive to the ECG sense signal inputs, and has variable rate control which is activated by module 81 in response to the physical activity sense signal supplied by accelerometer 40.

In operation, evaluation logic circuits 55 and 56 (FIG. 2) perform independent checks of the atrial rhythm status and the ventricular rhythm status, and fuzzy logic comparator 60 makes a comparison of these findings from the logic evaluations. The use of fuzzy logic, and avoidance of the linear mathematical approaches conventionally applied in the logic hardware and software of implantable defibrillators, is desirable because the inputs to the comparator display non-linearities, including those received from the cardiac activity (ECG) sense channels and the physical activity sense input from the accelerometer. The non-linearities present difficulties in performing standard linear mathematical computations. In contrast, fuzzy logic can more easily diagnose an atrial or ventricular rhythm disorder, and reach a decision, for example, of whether to shock the atrium to return the heart in atrial fibrillation or atrial flutter to sinus rhythm, or to pace the ventricle to break a ventricular tachycardia, or to apply a shock waveform to the ventricle to terminate ventricular fibrillation.

Thus, the combination of a conventional defibrillator with a DDD-R pacemaker in an implantable device offers advantages over the prior art. By stimulating the atrium at a constant rate, the occurrence of atrial dysrhythmias is reduced, especially when the stimulation is applied in conjunction with antiarrhythmic medications or beta-blockers. The hemodynamic improvement obtained by synchronization of the atrial and ventricular contractions further improves the overall cardiac performance of the patient, and therefore helps to reduce the occurrence of dysrhythmias. Further, the DDD-pacing renders the implanted device capable of sensing and responding to the status of the atrium, independent of ventricular sensing. Atrial stimulation is normally carried out to assure a constant or continuous rate of depolarizations, whether spontaneous or paced. The objective is to maintain AV synchrony, so that ventricular depolarizations are continuously synchronous with atrial depolarizations and each atrial beat followed sequentially by a ventricular beat. Sensing and pacing are also performed in the DDD mode in both the atrium and ventricle.

Figure 4:
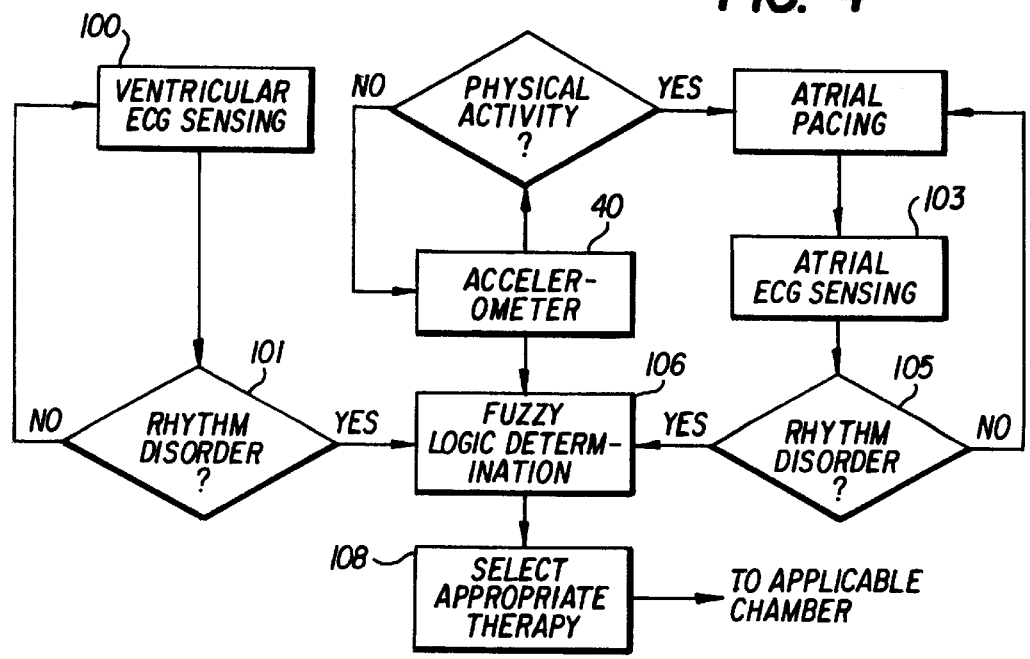
FIG. 4 is a simplified functional flow diagram of the operation of the implanted defibrillator using fuzzy logic for analysis and diagnosis.

A method of treating any of multiple cardiac rhythm disorders with only the single implanted medical interventional device includes device-implemented steps illustrated in the flow diagram of FIG. 4. Cardiac activity of the ventricle is sensed at 100 to detect whether rhythm disorders are present at 101. Concurrently, atrial activity is sensed at 103 to detect rhythm disorders in that chamber at 105. When a dysrhythmia is detected in the atrium or ventricle, a diagnosis is performed to identify the heart chamber in which it originated, and an appropriate therapy is then selected and delivered to the heart chamber identified as the origin of the detected disorder.

Discrimination between the detected atrial and ventricular rhythm disorders is performed by use of the device fuzzy logic at 106. Preferably, the ECG signal of the respective chamber is analyzed with respect to at least one of the attributes of cycle length, cycle length variation, amplitude, amplitude variation, and frequency content of the signal. Current ECG data from the atrial and ventricular chambers is compared by the fuzzy logic with previous ECG data for the respective chambers, to assess trend and first in/first out data of the individual ECG signals, for classifying the dysrhythmia. If no dysrhythmia is present in the atrium, the implanted device continues pacing the atrium at a constant rate for AV synchronization. If a dysrhythmia is detected in either chamber (or in both), an appropriate therapy is selected at 108 from among a plurality of electrical waveform therapies, to treat the detected disorder.

The atrium is paced continuously at the preselected fixed rate, except when the physical activity sensor (accelerometer 40) detects activity on the part of the patient which requires an applicable increase in the pacing rate, or when a different therapy regimen is selected and delivered to treat the detected disorder. Separate single transvenous cardiac leads are implanted for sensing, pacing, cardioverting and defibrillating the atrial and ventricular chambers, respectively.

Although a preferred embodiment and method have been disclosed herein, it will be apparent to those skilled in the art from a consideration of the foregoing description that variations and modifications of the described embodiment and method may be made without departing from the true spirit and scope of the invention. Accordingly, it is intended that the invention shall be limited only to the extent required by the appended claims and the rules and principles of applicable law.

What is claimed is:

1. An implantable medical interventional device having means for selectively supplying a plurality of therapeutic regimens to alleviate various ones of a plurality of cardiac rhythm disorders, including ventricular defibrillator means responsive to ventricular fibrillation of a patient's heart for defibrillating the ventricles of the heart, and an improvement to enhance recognition, discrimination and therapeutic treatment of cardiac rhythm disorders, said improvement comprising:

artificial pacing means for pacing the patient's heart including continuous sensing and responsive pacing of cardiac activity of both the atrial and ventricular chambers for monitoring the status of cardiac activity of the atrial and ventricular chambers and for maintaining atrioventricular synchrony of the patient's heart, and evaluation means operatively combining the artificial pacing means and the ventricular defibrillator means, for determining the existence of a particular rhythm disorder to identify and treat said particular rhythm disorder, said evaluation means including logic means responsive to signals developed by said atrial and ventricular sensing for comparing the atrial and ventricular signals to diagnose when the comparison is indicative of a cardiac rhythm disorder being experienced by the patient and based on said indication to prescribe an appropriate one of said plurality of therapeutic regimens to alleviate the diagnosed rhythm disorder.

2. The device of claim 1, wherein said pacing means includes:

a pulse generator for generating pulses at a predetermined adequate rate, detection means for detecting a parameter indicative of a physiological need of the patient for pacing at an atrial rate different from said predetermined adequate rate and producing a signal indicative of such physiological need, and pulse rate varying means responsive to said signal indicative of physiological need for controllably varying the rate at which pulses are generated by said pulse generator to adapt the paced atrial rate to a rate for satisfying said physiological need.

3. The device of claim 1, including:

a metal case housing at least a portion of the device for subcutaneous implantation in the patient's left chest area, said case constituting an electrode of the device for use in defibrillation.

4. The device of claim 1, including atrial defibrillator means having shock producing means responsive to detection of atrial fibrillation for applying a defibrillating shock to the atrium and, in conjunction with said artificial pacing means, to return the atrial rate to a predetermined adequate rate synchronized with the ventricular rate.

5. The device of claim 4, including:

electrical connector means for accepting a single atrial lead for atrial sensing, pacing, and defibrillation, and a single ventricular lead for ventricular sensing, pacing, and defibrillation.

6. The device of claim 5, including:

a single atrial lead and a single ventricular lead, each including at least a portion composed of an electrically conductive material of low polarization to permit detection of intrinsic rhythm in a respective chamber of the patient's heart despite presence of otherwise interfering polarization current on a respective one of said atrial and ventricular leads.

7. The device of claim 6, wherein said electrically conductive material is carbon.

8. The device of claim 6, wherein said electrically conductive material is carbon fiber.

9. An implantable medical interventional device having means for selectively supplying a plurality of therapeutic regimens to alleviate various ones of a plurality of cardiac rhythm disorders, including ventricular defibrillator means responsive to ventricular fibrillation of a patient's heart for use in defibrillating the ventricles of the heart, and an improvement to enhance recognition, discrimination and therapeutic treatment of cardiac rhythm disorders, said improvement comprising:

artificial pacing means for pacing the patient's heart including continuous sensing and responsive pacing of cardiac activity of both the atrial and ventricular chambers for monitoring the status of cardiac activity of the atrial as well as the ventricular chambers and for maintaining atrioventricular synchrony of the patient's heart;

evaluation means operatively combining the artificial pacing means and the ventricular defibrillator means, for determining the existence of a particular rhythm disorder to identify and treat the indicated rhythm disorder, said evaluation means including means for diagnosing an apparent atrial rhythm disorder from an atrial sensing signal; and detecting means for detecting the status of a physiological parameter of the patient other than ECG to verify or reject a diagnosis of atrial rhythm disorder by the diagnosing means from the atrial sensing signal.

10. The device of claim 9, wherein:

said detecting means comprises an accelerometer for detecting patient movement or position.

11. An implantable medical interventional device having means for selectively supplying a plurality of therapeutic regimens to alleviate various ones of a plurality of cardiac rhythm disorders, including ventricular defibrillator means responsive to ventricular fibrillation of a patient's heart for use in defibrillating the ventricles of the heart, and an improvement to enhance recognition, discrimination and therapeutic treatment of cardiac rhythm disorders, said improvement comprising:

artificial pacing means for pacing the patient's heart including continuous sensing and responsive pacing of cardiac activity of both the atrial and ventricular chambers for monitoring the status of cardiac activity of the atrial as well as the ventricular chambers and for maintaining atrioventricular synchrony of the patient's heart, and evaluation means operatively combining the artificial pacing means and the ventricular defibrillator means for developing generalized findings indicative of the existence of a particular rhythm disorder to identify and treat the indicated rhythm disorder, said evaluation means comprising fuzzy logic including means for discriminating between detected atrial and ventricular rhythm disorders to identify the heart chamber in which a detected disorder originates, and means for selecting a pacing, cardioverting or defibrillating therapy for delivery to the identified heart chamber.

12. An implantable medical interventional device having means for selectively supplying a plurality of therapeutic regimens to alleviate various ones of a plurality of cardiac rhythm disorders, including ventricular defibrillator means responsive to ventricular fibrillation of a patient's heart for use in defibrillating the ventricles of the heart, and an improvement to enhance recognition, discrimination and therapeutic treatment of cardiac rhythm disorders, said improvement comprising:

artificial pacing means for pacing the patient's heart including continuous sensing and responsive pacing of cardiac activity of both the atrial and ventricular chambers for monitoring the status of cardiac activity of the atrial as well as the ventricular chambers and for maintaining atrioventricular synchrony of the patient's heart, atrial defibrillator means responsive to the monitored status of the atrium as being indicative of atrial fibrillation for generating electrical therapy to defibrillate the atria, evaluation means operatively combining, the artificial pacing means, the atrial defibrillator means and the ventricular defibrillator means, for developing generalized findings indicative of the existence of a particular rhythm disorder to identify and treat the indicated rhythm disorder, and electrical connector means for accepting a single atrial lead for atrial sensing, pacing, and defibrillation, and a single ventricular lead for ventricular sensing, pacing, and defibrillation, said single atrial lead including a first defibrillating electrode adapted to be positioned in the right atrium and a second defibrillating electrode adapted to be positioned in the left pulmonary artery or the distal coronary sinus, when said atrial lead is implanted in the patient's heart.

13. An interventional medical device structured and adapted for implantation into a patient to diagnose cardiac rhythm disorders and selectively deliver any of a plurality of electrical waveform therapies to treat a sensed disorder, the device comprising:

ventricular therapy means for sensing and treating ventricular rhythm disorders, and atrial therapy means for sensing and treating atrial rhythm disorders, and including means to synchronize atrial and ventricular beats when atrial rhythm disorders are not present;

the ventricular therapy means and the atrial therapy means including means for defibrillating the respective ventricular and atrial chambers, ECG data storage means, and fuzzy logic means for comparing current ECG parameters with stored ECG parameters for enhancing the diagnosis to provide more precise rhythm disorder recognition and classification.

14. The device of claim 13, including:

means for separating atrial and ventricular ECG signals into attributes including amplitude of the ECG signal, amplitude relative to stored ECG signals, variation of ECG signal amplitudes, cycle length, variation of cycle length, morphology of ECG signal, and vector of an intracardiac ECG.

15. The device of claim 13, including:
a metal case for housing device components and for use as a defibrillation electrode.

16. A method of treating a plurality of cardiac rhythm disorders with a single medical interventional device implanted in a human patient, including the device-implemented steps of:
sensing both atrial and ventricular rhythm disorders of the patient's heart and responding with automatic therapeutic treatment from the device by application to a heart chamber of an appropriate therapy regimen selected from pacing, cardioverting and defibrillating electrical waveforms of predetermined type and energy content, and
selecting the appropriate therapy regimen and the heart chamber to which it should be applied by evaluating atrial and ventricular ECG signals to develop therefrom generalized findings indicative of existence of a specific rhythm disorder and, from the generalized findings, to identify whether a specific ventricular rhythm disorder originated in the atrium or the ventricle.

17. The method of claim 16, further including:
pacing the atrium at a selected rate except when a sensed disorder requires a different therapy regimen to be applied to the atrium.

18. The method of claim 17, further including:
detecting patient physical activity and responding thereto by adjusting the pacing rate of both atrium and ventricle to satisfy the physiological need of the patient for a faster rate during the physical activity.

19. The method of claim 18, further including:
using the detection of patient physical activity to confirm or to reject the indication of specific rhythm disorder from the evaluation.

20. A method of treating a plurality of cardiac rhythm disorders with a single medical interventional device implanted in a human patient, including the device-implemented steps of:
sensing both atrial and ventricular rhythm disorders of the patient's heart and responding with automatic therapeutic treatment from the device by application to a heart chamber of an appropriate therapy regimen selected from pacing cardioverting and defibrillating electrical waveforms of predetermined type and energy content, and
selecting the appropriate therapy regimen and the heart chamber to which it should be applied by evaluating atrial and ventricular ECG signals to develop therefrom generalized findings indicative of existence of a specific rhythm disorder and, from the generalized findings, to identify the heart chamber in which the specific rhythm disorder originated, including performing the step of evaluating the atrial and ventricular ECG signals by applying a fuzzy logic comparison of current ECG parameters with stored ECG parameters for enhanced recognition and classification of rhythm disorders.

21. An implantable defibrillator device, comprising:
a DDD-R mode pacemaker having electrode means for continuously sensing and pacing atrial and ventricular chambers to maintain AV synchrony, and sensor means to generate a rate adaptive pacing signal to vary stimulation rate of a patient's heart according to the patient's need,
defibrillator means in combination with said pacemaker, for treating arrhythmias including fibrillation; and
evaluation means operatively combining said DDD-R pacemaker and said defibrillator means for developing generalized findings indicative of the apparent presence of a specific arrhythmia of the atrial or ventricular chamber from sensed signals therefrom by which to assess appropriate treatment therapy for the indicated arrhythmia.

22. The implantable defibrillator device of claim 21, wherein said pacemaker includes means for limiting ventricular rate response of the heart to avoid an excessively high ventricular rate attributable to an atrial arrhythmia.

23. The device of claim 21, wherein said sensor means is an accelerometer.

24. The device of claim 23, wherein said device is encompassed in a metallic housing, and said accelerometer is isolated from said metallic housing.

25. An implantable medical interventional device having means for selectively supplying a plurality of therapeutic regimens to alleviate various ones of a plurality of cardiac rhythm disorders, including ventricular defibrillator means responsive to ventricular fibrillation of a patient's heart for use in defibrillating the ventricles of the heart, and an improvement to enhance recognition, discrimination and therapeutic treatment of cardiac rhythm disorders, said improvement comprising:
artificial pacing means for pacing the patient's heart including continuous sensing and responsive pacing of cardiac activity of both the atrial and ventricular chambers for monitoring the status of cardiac activity of the atrial as well as the ventricular chambers and for maintaining atrioventricular synchrony of the patient's heart, said artificial pacing means including atrial sensing means for sensing electrical activity of the atrium of the patient's heart to produce a signal representative of the atrial activity and ventricular sensing means for sensing ventricular electrical activity of the patient's heart to produce a signal representative of the ventricular activity, and pacing generator means for stimulating the atrium at a predetermined adequate rate;
said pacing generator means including a pulse generator for generating pulses at said predetermined adequate rate, detection means for detecting a parameter indicative of a physiological need of the patient for pacing at an atrial rate different from said predetermined adequate rate and producing a signal indicative of such physiological need, and pulse rate varying means responsive to said signal indicative of physiological need for controllably varying the rate at which pulses are generated by the pulse generator to adapt the paced atrial rate to a rate for satisfying said physiological need; and
evaluation means operatively combining the artificial pacing means and the ventricular defibrillator means, for developing generalized findings indicative of the existence of a particular rhythm disorder to identify and treat the indicated rhythm disorder, said evaluation means including logic means responsive to the atrial and ventricular sensing means signals for comparing the atrial rate to the ventricular rate to diagnose when the comparison is indicative of a cardiac rhythm disorder being experienced by the patient and based thereon to prescribe an appropriate one of said plurality of therapeutic regimens to alleviate the diagnosed cardiac rhythm disorder.

* * * * *